US010772925B2

(12) United States Patent
Giversen et al.

(10) Patent No.: US 10,772,925 B2
(45) Date of Patent: Sep. 15, 2020

(54) COMPOSITION FOR ENHANCING SEMEN QUALITY IN A MALE SUBJECT

(71) Applicant: NERTHUS APS, Lejre (DK)

(72) Inventors: Ina Giversen, Lejre (DK); Henrik Jakobsen, Lejre (DK)

(73) Assignee: NERTHUS APS, Lejre (DK)

( * ) Notice: Subject to any disclaimer, the term of this patent is extended or adjusted under 35 U.S.C. 154(b) by 399 days.

(21) Appl. No.: 14/896,122

(22) PCT Filed: Jun. 6, 2014

(86) PCT No.: PCT/EP2014/061851
§ 371 (c)(1),
(2) Date: Dec. 4, 2015

(87) PCT Pub. No.: WO2014/195469
PCT Pub. Date: Dec. 11, 2014

(65) Prior Publication Data
US 2016/0120930 A1 May 5, 2016
US 2016/0317598 A2 Nov. 3, 2016

(30) Foreign Application Priority Data

Jun. 7, 2013 (EP) .................................... 13171033

(51) Int. Cl.
| *A61K 36/906* | (2006.01) |
| *A61K 36/00* | (2006.01) |
| *A61K 36/9062* | (2006.01) |
| *A23L 5/00* | (2016.01) |
| *A61K 36/185* | (2006.01) |
| *A61K 36/45* | (2006.01) |
| *A61K 36/736* | (2006.01) |
| *A23L 31/00* | (2016.01) |
| *A61P 15/08* | (2006.01) |
| *A61K 36/61* | (2006.01) |
| *A61K 36/738* | (2006.01) |
| *A61K 9/16* | (2006.01) |
| *A61K 31/05* | (2006.01) |
| *A61K 31/235* | (2006.01) |
| *A61K 31/7048* | (2006.01) |
| *A23L 33/105* | (2016.01) |

(52) U.S. Cl.
CPC ............ *A61K 36/9062* (2013.01); *A23L 5/00* (2016.08); *A23L 31/00* (2016.08); *A23L 33/105* (2016.08); *A61K 9/16* (2013.01); *A61K 31/05* (2013.01); *A61K 31/235* (2013.01); *A61K 31/7048* (2013.01); *A61K 36/185* (2013.01); *A61K 36/45* (2013.01); *A61K 36/61* (2013.01); *A61K 36/736* (2013.01); *A61K 36/738* (2013.01); *A61P 15/08* (2018.01); *A23V 2002/00* (2013.01)

(58) Field of Classification Search
None
See application file for complete search history.

(56) References Cited

U.S. PATENT DOCUMENTS

| 2002/0086906 A1 | 7/2002 | Weidner et al. |
| 2003/0157204 A1* | 8/2003 | Weidner .................. A61K 8/97 424/756 |
| 2005/0238737 A1 | 10/2005 | Jean et al. |

FOREIGN PATENT DOCUMENTS

| JP | 408070829 A | * | 3/1996 |
| JP | 2005179285 A | * | 7/2005 |
| JP | 2011225626 A | * | 11/2011 |

OTHER PUBLICATIONS

International Preliminary Report of Patentability dated Jun. 12, 2015 for International Application No. PCT/EP2014/061851.
Ahmed, K.A., et al., "Assessment of a Polyherbal Ayurevdic Medicine for Sexual Activity in Rats," Indian Drugs, Jan. 1, 1999, pp. 576-582, XP055141960.
Blount, J.D., et al., "Antioxidants, Showy Males and Sperm Quality," Ecology Letters, vol. 4, No. 5, Sep. 1, 2001, pp. 393-396, XP055141959, ISSN: 1461-023X, DOI: 10.1046/j. 1461-0248.2001. 00255.x.
Jurenka, J., "Therapeutic Application of Pomegranate (Punica Granatum L): A Review," Alternative Medicine Review, vol. 13, No. 2, Jan. 1, 2008, pp. 128-144, XP55129347.
Singh, B., et al., "Pharmacological Potential of Plant Used as Aphrodisiacs," International Journal of Pharmaceutical Sciences Review and Research, vol. 5, Issue 1, Nov.-Dec. 2010, Article-016; ISSN 0976-044X.
Turk, G., et al., "Effects of Pomegranate Juice Consumption on Sperm Qualitym Spermatogenic Cell Density, Antioxidant Activity and Testosterone Level in Male Rats," Clinical Nutrition, Churchill Livingstone, London, GB, vol. 27, No. 2, Apr. 1, 2008, pp. 289-296, XP022584804, ISSN: 0261-5641, DOI: 10.1016/J.CLNU.2007.12. 006.
Bhat, M.M., et al., "Standardization of Recipe for the Preparation of Dried Wild Pomegranate (anardana)-Long Gourd Appetizer," Journal of Hill Agriculture 4(a): 16-21, Jan.-Jun., 2013, vol. 4, No. 1, Jun. 1, 2013, ISSN:0976-7606.

* cited by examiner

*Primary Examiner* — Michael Barker
*Assistant Examiner* — Randall Winston
(74) *Attorney, Agent, or Firm* — Fox Rothschild LLP; Carol E. Thorstad-Forsyth

(57) ABSTRACT

The present invention relates to a composition comprising a dry preparation of *Alpinia galanga* (L.) Willd (Zingiberaceae) or *Alpinia conchigera* Griff and a plant extract comprising compounds with anti-oxidative activity, such as an extract of *Punica granatum*. Also disclosed herein is a method of improving semen quality by administering said composition to a male subject in need thereof.

19 Claims, 4 Drawing Sheets

FIG. 2

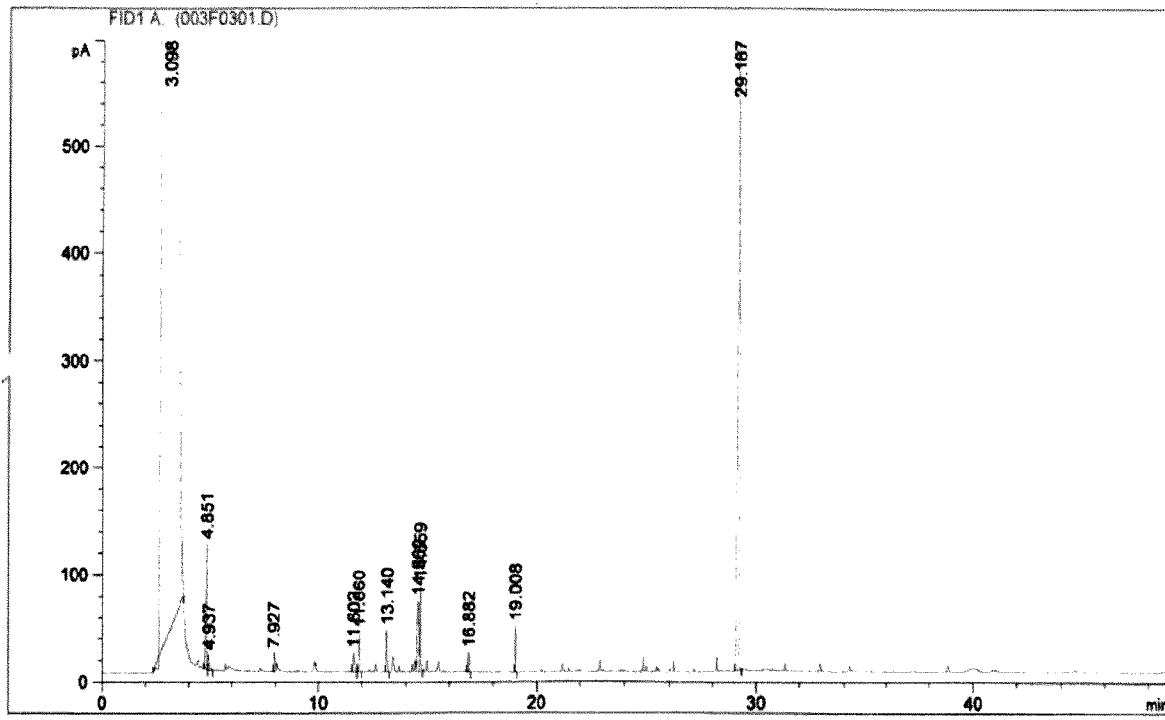

```
===================================================================
                          Area Percent Report
===================================================================

Sorted By                 :     Signal
Calib. Data Modified      :     6/25/2012 2:26:29 PM
Multiplier:                     :      1.0000
Dilution:                       :      1.0000
Use Multiplier & Dilution Factor with ISTDs Signal 1: FID1 A, Peak RetTime Type   Width     Area       Area     Name
 #   [min]          [min]     [pA*s]      %
----|-------|------|--------|----------|---------|----------------
  1   3.098 BB S   0.3706  2.22586e6   99.74472  ?
  2   4.851 BV     0.0436   369.29840   0.01655  ?
  3   4.937 VB     0.0584    60.10364   0.00269  ?
  4   7.927 BV     0.0551    72.09885   0.00323  ?
  5  11.602 BB     0.0643    82.56042   0.00370  ?
  6  11.860 BB     0.0578   153.30005   0.00687  ?
  7  13.140 BB     0.0468   125.68452   0.00563  ?
  8  14.569 VV     0.0622   302.83954   0.01357  ?
  9  14.659 VV     0.0452   254.50020   0.01140  ?
 10  16.882 VB     0.0450    52.08237   0.00233  ?
 11  19.008 BB     0.0383   104.53390   0.00468  ?
```

COMPOSITION FOR ENHANCING SEMEN QUALITY IN A MALE SUBJECT

CROSS-REFERENCE TO RELATED APPLICATION

The present application is a U.S. National Phase of International Patent Application Serial No. PCT/EP2014/061851, filed on Jun. 6, 2014, which claims priority to European Patent Application No. 13171033.7, filed Jun. 7, 2013, the disclosures of which are incorporated herein by reference in their entireties.

FIELD OF INVENTION

The present invention relates to a composition comprising a dry preparation of *Alpinia galanga* (L.) Willd (Zingiberaceae) or *Alpinia conchigera* Griff and a plant extract comprising compounds with anti-oxidative activity, such as an extract of *Punica granatum*. Also disclosed herein is a method of improving semen quality by administering said composition to a male subject in need thereof.

BACKGROUND OF INVENTION

Oligospermia (low amount of sperm in the semen) or azoospermia (no measurable amount of sperm in the semen) are medical conditions that are responsible for up to 20% of infertility situations in males. Semen quality may be measured in a number of ways. The total number of motile spermatozoa or total motile sperm count (TMSC) is regarded as one of the sperm characteristics most closely related to pregnancy. A semen analysis typically measures the number of sperm per millilitre of ejaculate, and analyses the morphology and motility of the sperm. The typical ejaculate of a healthy, physically mature young adult male of reproductive age with no fertility-related problems usually contains 300-500 million spermatozoa, though only a couple hundred survive in the acidic environment of the vagina to be candidates for successful fertilization. Other parameters reflective of semen quality are the concentration of white blood cells, the level of fructose in the semen, and the volume, pH, and liquefaction time of the ejaculate. A number of factors may influence the accuracy of semen analysis results, and results for a single man may have a large amount of natural variation over time. There has been evidence for a general decline in sperm counts in Europe and the USA between 1983 and 1990.

To date no clinically documented and officially approved treatment exists for the improvement of semen quality. Instead, microsurgical procedures or in vitro fecundation with the semen from the subject or with donor semen are often the only alternatives offered to subjects suffering from low semen quality. Thus there is a need for methods of improving semen quality without surgery so that men in need thereof may conceive children.

SUMMARY OF INVENTION

The present invention provides a composition comprising a dry preparation I of *Alpinia galanga* or *Alpinia conchigera* and a plant extract II comprising compounds with anti-oxidative activity. Also disclosed is a method for improving semen quality by administration of such a composition to a male subject.

Pomegranate (*Punica granatum* L., Punicaceae) is a shrub or tree mainly cultivated in areas of the Near East, India, Spain, Israel and USA. The fruit is consumed fresh or processed to obtain juice. In modern herbal medicine pomegranate fruit is used among other purposes as a cardioprotective remedy, against hyperlipidemia and against recurring prostate cancer.

The pomegranate fruit consists of a leathery pericarp, containing numerous arils, each a single seed surrounded by a translucent juice-containing sac. Thin membranes extend into the interior of the fruit from the pericarp, providing a latticework for suspending the arils. Thus, the fruit itself gives rise to three parts: the seeds, about 3% of the weight of the fruit, and themselves containing about 20% oil, the juice, about 30% of the fruit weight, and the peel (pericarp) which also includes the interior network of membranes.

The beneficial effects of pomegranate juice are attributed to its antioxidant constituents, including: hydrolysable tannins (among these ellagitannins such as punicalagin isomers), anthocyanins, ellagic acid and its derivatives and vitamin C. In commercial pomegranate juice, the water-soluble punicalagins are the most important antioxidant compounds, rendering commercial products up to twice as strong antioxidants as handpressed juice. Punicalagins are abundant in the pericarp and, during commercial processing, are extracted into pomegranate juice in significant quantities.

The effect of pomegranate juice or extract on semen quality has been investigated in two in vivo studies performed on mice and rats. No studies on the effects in humans have been published previously. In one study performed on rats, commercial, pasteurized pomegranate juice caused an increase in sperm motility (27%) at a daily dose of 3.6 ml pomegranate juice/kg bw for seven weeks (Turk et al., 2008). Similar effects, although weaker, were seen at lower doses. The study reports no effect of pomegranate on the reproductive organs weight. In a study on rats, an ethanolic extract of pomegranate did not affect spermatogenesis, daily sperm production or epididymal sperm number in untreated rats, but slightly reduced the negative effects on these parameters in rats treated with lead acetate (Leiva et al., 2011).

No serious adverse effects have been reported in clinical studies as far as known. Doses of 50 ml pomegranate juice/day for several years or 240 ml/day for several months have been well tolerated.

*Alpinia galanga* (L.) Willd. or greater galangal belongs to the Zingiberaceae (ginger family). The plant is native to Indonesia, Malaysia and India. The rhizome is used as a condiment in some areas. The plant is traditionally used for the treatment of inflammatory conditions, respiratory infections, cancer, dyspepsia, colic and sea sickness and as a tonic and an aphrodisiac. *Alpinia conchigera* is a closely related species native to Thailand, Malaysia and India.

The rhizome of *A. galanga* comprises several phenylpropanoids with pharmacological activity, including 1',S-1'-acetoxychavicol acetate (ACA), 1',S-1'-acetoxyeugenol acetate (AEA) and 1',S-1'-hydroxychavicol acetate (HCA). The rhizome also contains essential oil with 1,8-cineole being a major constituent. High levels of magnesium, calcium, potassium and manganese are also present.

The ethanolic extract of the rhizome of *A. galanga* has shown several sperm-improving effects in mice at a daily dose of 100 mg/kg bw for three months. Both sperm motility and sperm concentration increased slightly, but significantly, with the increase in sperm motility being most pronounced (Qureshi et al., 1992). The study reports no effect on the percentage of abnormal spermatozoa.

Another study on the effect of the alcoholic extract of the rhizome of *A. galanga* in rats showed that administration of a daily dose of 200 mg extract/kg bw caused a significant increase in serum testosterone level in 15 days (Islam et al., 2000).

No serious adverse effects are known in relation to consumption of the ethanolic extract of the rhizome of *A. galanga*. A chronic dose of 100 mg ethanolic extract/kg bw is well tolerated in mice (Qureshi et al., 1992).

To date the effects of preparations of *P. granatum* and/or *A. galanga* have not been studied in relation to human semen quality.

BRIEF DESCRIPTION OF DRAWINGS

FIG. 2: GC chromatogram from fresh *Alpinia galanga* rhizomes.

DETAILED DESCRIPTION OF DRAWINGS

Figure 1:
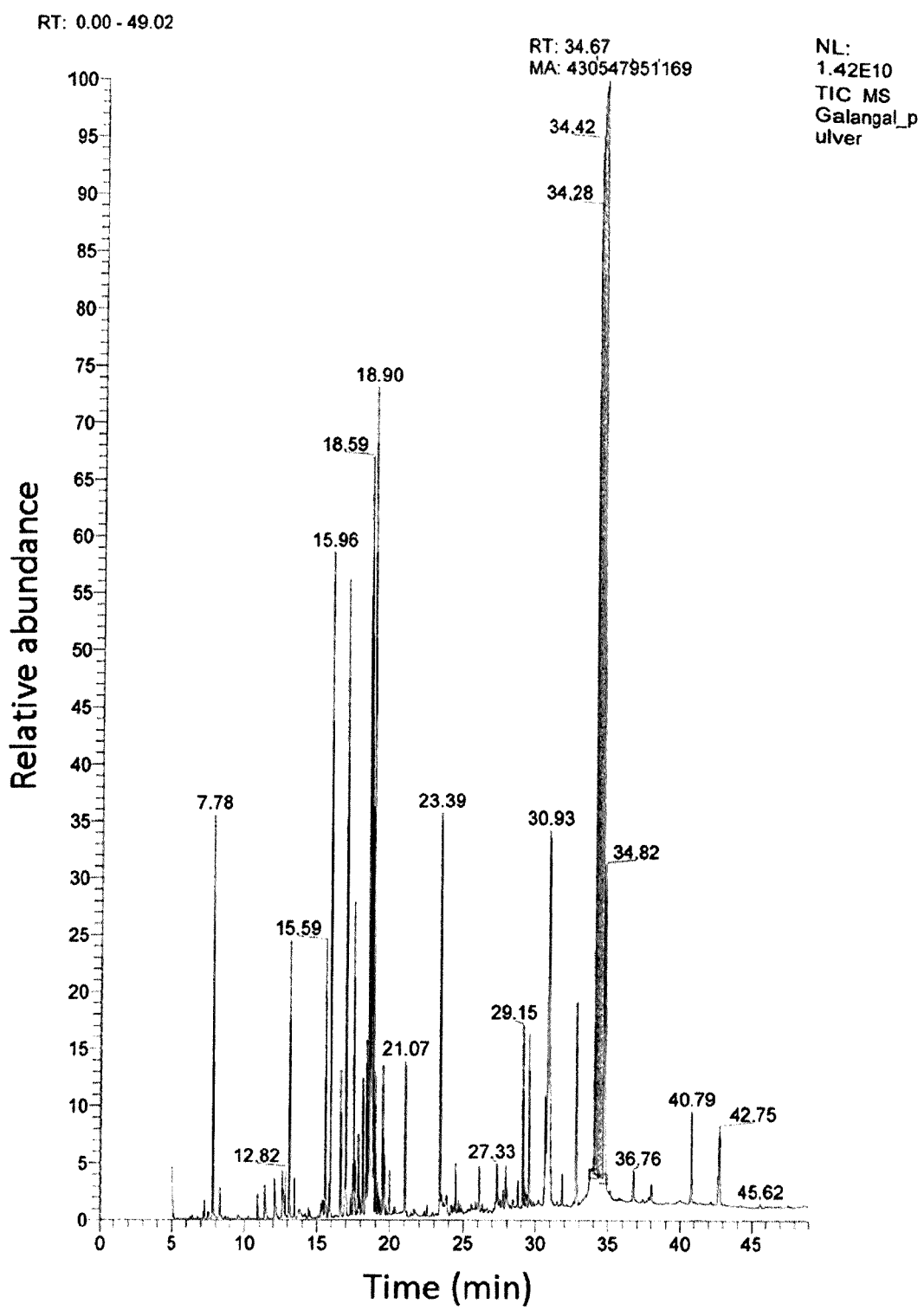
FIG. 1: GC chromatogram of a dry preparation of freeze-dried *Alpinia galanga* rhizomes.

FIG. 1. GC chromatogram of a dry preparation of *Alpinia galanga* freeze-dried rhizomes. The dominating compound at rt. 34.2-34.4 min is ACA (1'S-1'-acetoxychavicol acetate) identified by mass spectra of the compound in the extract combined with spectra and retention times of the ACA standard.

FIG. 2. GC chromatogram of an extract of fresh *Alpinia galanga* rhizomes. The dominating compound at rt. 29.18 min is ACA (1'S-1'-acetoxychavicol acetate) identified by mass spectra of the compound in the extract combined with spectra and retention times of the ACA standard. Slightly different conditions (oven programme and column flow) has been used for this chromatogram compared to the chromatograms presented in FIGS. 1 and 3.

Figure 3:
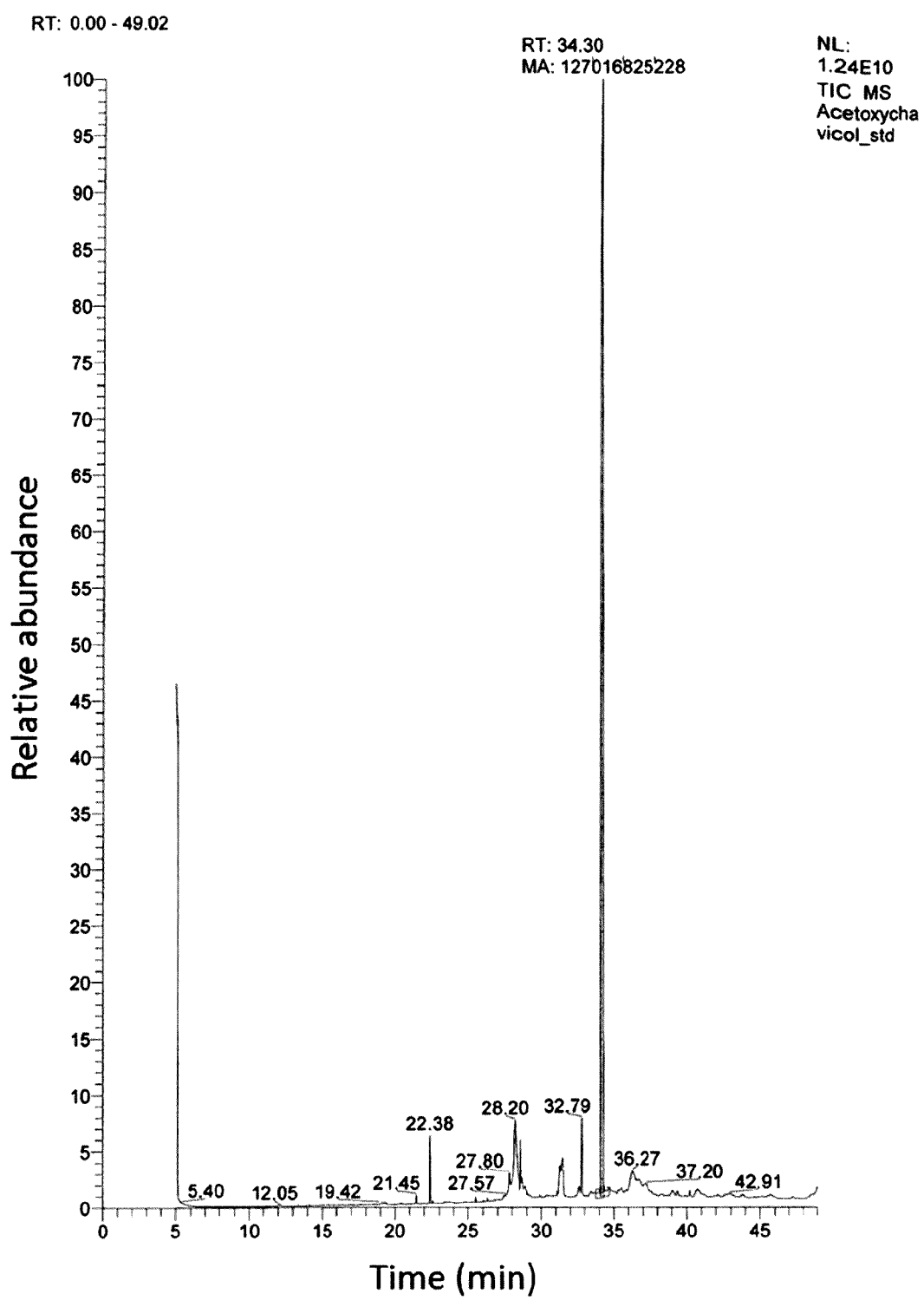
FIG. 3: GC chromatogram of external ACA standard.

FIG. 3. GC chromatogram of ACA (1'S-1'-acetoxychavicol acetate) standard supplied by Phytolab. The GC parameters are similar to those used for the chromatogram presented in FIG. 1.

Figure 4:
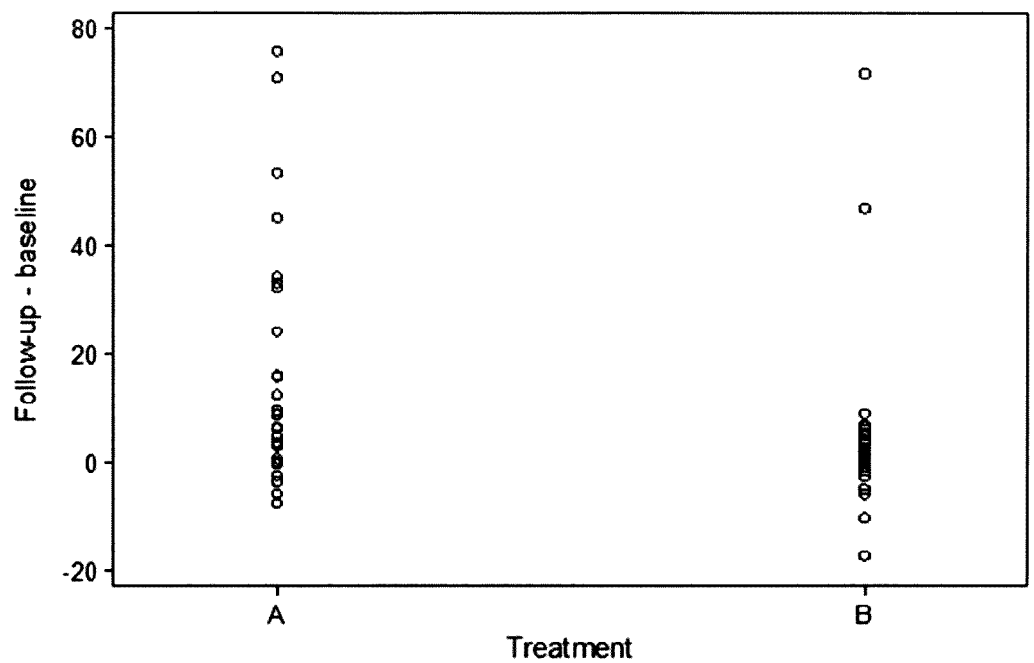
FIG. 4: Increases in TMSC from baseline to follow-up for each participant in the plant group and placebo group.

FIG. 4. Plot of the differences in TMSC (Total motile sperm count) from baseline to follow up for each participant in the treatment group (A) receiving the *Alpinia galanga* preparation and *Punica granatum* pomace extract, and placebo group (B). Follow up-baseline (Y-axis) represents the calculated differences in TMSC between the Follow up TMSCs following 90 days of administration of either the dry preparation of *A. galanga* and the *P. granatum* extract (group A) or the placebo (group B) and the corresponding TMSCs prior to administration.

DETAILED DESCRIPTION OF THE INVENTION

Definitions

1"S-1"-acetoxychavicol acetate (ACA)

1"S-1"-acetoxychavicol acetate (ACA) is a semi-volatile phenylpropanoid. Under typical hydrolytic conditions in water or aqueous ethanol, in particular if raised temperatures are imposed on the extract, ACA may be partly or fully converted to 1'-hydroxychavicol acetate and/or p-acetoxycinnamic alcohol and/or p-coumaryl diacetate.

Aerobic Microorganism

An aerobic organism or aerobe is an organism that can survive and grow in an oxygenated environment.

*Alpinia conchigera*

*Alpinia conchigera* Griff. belongs to the Zingiberaceae (ginger family). The plant is native to Thailand, Malaysia and India.

*Alpinia galanga*

*Alpinia galanga* (L.) Willd. or greater galangal belongs to the Zingiberaceae (ginger family). The plant is native to Indonesia, Malaysia and India. The plant grows from rhizomes in clumps of stiff stalks up to two meters in height with abundant long leaves and panicles of greenish white flowers.

Anhydrous/Dry

As understood herein, the terms 'anhydrous' or 'dry' refer to a substance with a water content less than 15%.

Anti-Oxidative Activity

Anti-oxidative activity is the activity exerted by antioxidants, i.e. molecules that inhibit the oxidation of other molecules. Oxidation is a chemical reaction that transfers electrons or hydrogen from a substance to an oxidizing agent. Oxidation reactions can produce free radicals. In turn, these radicals can start chain reactions. When the chain reaction occurs in a cell, it can cause damage or death to the cell. Antioxidants terminate these chain reactions by removing free radical intermediates, and inhibit other oxidation reactions. Antioxidants get oxidised in the process. They are often reducing agents such as thiols, ascorbic acid, or polyphenols.

Binder

The term "binder" refers to an excipient, which ensures cohesion within tablets and granules and other formulations. The use of a binder allows formulation with sufficient mechanical strength.

Down-Sizing

As understood herein, the term "down-sizing" refers to a process wherein a preparation such as a powder undergoes a size reduction. For example, down-sizing of a powder results in a powder wherein the final size of the particles of the powder is reduced. Down-sizing can be performed in conjunction with milling, some millers being equipped with screens which only allow passage of particles smaller than the size of the screen's opening.

Ellagitannins

Ellagitannins are a diverse class of hydrolyzable tannins, a type of polyphenol formed primarily from the oxidative linkage of galloyl groups in 1,2,3,4,6-pentagalloyl glucose. Ellagitannins have been investigated in cells and animals in laboratories for antioxidant, anti-cancer, antiviral, antimicrobial, and anti-parasite activities, as well as their ability to regulate blood glucose. The pomegranate ellagitannins, which include punicalagin isomers, are ellagitannins found in the fruit, rind (peel), bark or heartwood of pomegranates. Punicalagins are also found to be important for commercial pomegranate juice's antioxidant and health benefits. Examples of ellagitannins found in pomegranates are: punicalins, punicalagins A and B, punicalin isomers.

Freeze-Drying

Freeze-drying as understood herein relates to a procedure for drying a solid compound such as rhizomes of *A. galanga*. Freeze-drying procedures as understood herein may comprise the steps of:

i) Freezing the rhizomes to a temperature of about −18 or −20° C.;

ii) Applying vacuum until the pressure is stable and in the range of 1.5 to 1.7 mb; the pressure may be maintained stable by supplying e.g. nitrogen;
iii) Increasing the temperature to start the drying process;
iv) Eliminating the vacuum.

Thus, freeze-drying comprises the steps necessary to allow sublimation of the water comprised in the material to be freeze-dried, i.e. the rhizomes.

Granulate/Granulation

A granulate or granular material is a conglomeration of discrete solid, macroscopic particles characterized by a loss of energy whenever the particles interact. The constituents that compose granular material must be large enough such that they are not subject to thermal motion fluctuations. Thus, the lower size limit for grains in granular material is about The term 'granulation' refers to the process of forming a granulate.

Oxygen-Free Gas

An oxygen-free gas is to be construed as referring to a gas mixture comprising levels of oxygen so low that the growth of aerobic microorganisms is inhibited. Typically, levels of oxygen in an essentially oxygen-free gas are less than 3%.

Pharmacological Activity

Pharmacological activity refers to the effects of a drug on living matter. When a drug is a complex chemical mixture, this activity is exerted by the substance's active ingredient or pharmacophore but can be modified by the other constituents. Activity is generally dosage-dependent.

Phenylpropanoids

Phenylpropanoids are a diverse family of organic compounds that are synthesized by plants from the amino acid phenylalanine. Their name is derived from the six-carbon, aromatic phenyl group and the three-carbon propene tail of cinnamic acid, which is synthesized from phenylalanine in the first step of phenylpropanoid biosynthesis. Phenylpropanoids are found throughout the plant kingdom, where they serve as essential components of a number of structural polymers, provide protection from ultraviolet light, defend against herbivores and pathogens, and mediate plant-pollinator interactions as floral pigments and scent compounds. Three of the phenylpropanoids found in *Alpinia galanga* are 1'S-1'-acetoxychavicol acetate (ACA), 1'S-1'-acetoxyeugenol acetate (AEA) and V-hydroxychavicol acetate (HCA).

Powder/Pulverisation

A powder is a dry, bulk solid composed of a large number of very fine particles that may flow freely when shaken or tilted. The term 'pulverisation' refers to the process of transforming a solid substance into a powder, e.g. by milling.

*Punica granatum*

Pomegranate (*Punica granatum* L., Punicaceae) is a shrub or tree mainly cultivated in areas of the Near East, India, Spain, Israel and USA. The fruit is consumed fresh or processed to obtain juice. In modern herbal medicine pomegranate fruit is used among other purposes as a cardioprotective remedy, against hyperlipidemia and against recurring prostate cancer.

The pomegranate fruit consists of a leathery pericarp, containing numerous arils, each a single seed surrounded by a translucent juice-containing sac. Thin membranes extend into the interior of the fruit from the pericarp, providing a latticework for suspending the arils. Thus, the fruit itself gives rise to three parts: the seeds, about 3% of the weight of the fruit, and themselves containing about 20% oil, the juice, about 30% of the fruit weight, and the peel (pericarp) which also includes the interior network of membranes.

Punicalagins

Punicalagins A and B are a subclass of ellagitannins found to be important for commercial pomegranate juice's antioxidant and health benefits. Punicalagins are also found in other plants of the Combretaceae family: in the leaves of *Terminalia catappa* L., in the fruits of *Terminalia citrina* (Gaertn.) Roxb., in the roots of *Terminalia macroptera* Guill. & Perr., in the leaves of *Terminalia myriocarpa* Van Heurck & Mull. Arg., in the leaves of *Terminalia oblongata* F. Muell., in the leaves of *Combretum molle* R. Br. ex G. Don. and in the leaves of *Lumnitzera racemosa* Willd.

Punicalins

Punicalin is an ellagitannin. The term punicalins as understood herein relates to punicalins A and B as well as punicalin isomers.

Punicosides

As understood herein, the term punicosides refers to the punicalagins and punicalins, including punicalagin A and B, punicalins A and B and punicalin isomers.

Rhizome

A rhizome is a modified subterranean stem of a plant that is usually found underground, often sending out roots and shoots from its nodes.

Semen

Semen, also known as seminal fluid, is an organic fluid that may contain spermatozoa. It is secreted by the gonads (sexual glands) and other sexual organs of male or hermaphroditic animals and can fertilize female ova.

Semen Quality

Semen quality is a measure of the ability of semen to accomplish fertilization. Thus, it is a measure of fertility in a male subject. Semen quality involves both sperm quantity and quality. Decreased semen quality is a major factor of male infertility. Semen quality can be assessed by semen analyses. Examples of parameters measured in a semen analysis are: sperm count, motility, morphology, volume, fructose level and pH.

Sperm Motility

This term refers to the ability of spermatozoa to move forward. In the present context, the term is to be understood as referring also to the motility grade, where the motility of sperm are divided into four different grades:

Grade a: Sperm with progressive motility. These are the strongest and swim fast in a straight line.

Grade b: (non-linear motility): These also move forward but tend to travel in a curved or crooked motion.

Grade c: These have non-progressive motility because they do not move forward despite the fact that they move their tails.

Grade d: These are immotile and fail to move at all.

Spermatogenesis

Spermatogenesis is the process by which male primordial germ cells called spermatogonia undergo meiosis, and produce a number of cells termed spermatozoa. The initial cells in this pathway are called primary spermatocytes.

Total Motile Sperm Count (TMSC)

Total motile sperm count (TMSC) or Total motile spermatozoa (TMS) is a combination of sperm count, motility and volume, measuring how many million sperm cells in an entire ejaculate are motile. The TMSC is defined as: ejaculate volume.times.spermatozoa concentration.times.percentage of motile spermatozoa.

Volatility and Semi-Volatility

Volatility is the tendency of a substance to vaporize. Volatility is directly related to a substance's vapour pressure. At a given temperature, a substance with higher vapour pressure vaporizes more readily than a substance with a lower vapour pressure. Volatile compounds are compounds that have a high vapour pressure at ordinary, room-temperature conditions. Their high vapour pressure results from a low boiling point, which causes large numbers of molecules to evaporate or sublimate from the liquid or solid form of the compound and enter the surrounding air. A semi-volatile compound is a compound which has a boiling point higher than water and which may vaporize when exposed to temperatures above room temperature.

DETAILED DESCRIPTION OF THE INVENTION

The present invention relates to a composition comprising a dry preparation I of *Alpinia galanga* or *Alpinia conchigera* rhizomes and an extract II comprising compounds with anti-oxidant activity. Within the scope of the invention are also compositions comprising a dry preparation I, comprising essentially all the semi-volatile and non-volatile compounds of *Alpinia galanga* or *Alpinia conchigera* rhizomes. Using such a composition surprisingly results in an average increase in total motile sperm count of up to 74%.

Dry Preparation I

The dry preparation I is obtainable from *Alpinia galanga* or *Alpinia conchigera*, preferably by the method comprising the steps of:
i) providing non-dried rhizomes of *Alpinia galanga* or *Alpinia conchigera*;
ii) freeze-drying said rhizomes for a duration such that the water content of said rhizomes is below 15%;
iii) pulverizing said freeze-dried rhizomes at a temperature lower than 50° C.; said dry preparation comprising essentially all the non-volatile and semi-volatile compounds of *Alpinia galanga* or *Alpinia conchigera*. The dry preparation I comprises essentially all the non-volatile compounds and semi-volatile compounds of *Alpinia galanga* or *Alpinia conchigera*.

Preferred methods for producing the dry preparation I of *Alpinia galanga* or *Alpinia conchigera* result in a dry preparation I comprising essentially all the semi-volatile and non-volatile compounds of *Alpinia galanga* or *Alpinia conchigera*. The dry preparation I may also comprise volatile compounds of *A. galanga* or *A. conchigera*. The compounds which may be comprised in the dry preparation I include, but are not limited to: i) phenylpropanoids, including, but not limited to, 1'S-1'-acetoxychavicol acetate (ACA), 1'S-1'-acetoxyeugenol acetate (AEA) and 1'S-1'-hydroxychavicol acetate (HCA); ii) essential oils, including, but not limited to, 1,8-cineole; iii) minerals, including, but not limited to, magnesium, calcium, potassium and manganese. The dry preparation I may also comprise degradation products of the compounds present in fresh *A. galanga* or *A. conchigera* rhizomes, such as, but not limited to: 1'-hydroxychavicol acetate, p-acetoxycinnamic alcohol, p-coumaryl diacetate. The invention further relates to a dry preparation I comprising one or more of the following: phenylpropanoids, such as 1'S-1'-acetoxychavicol acetate (ACA), 1'S-1'-acetoxyeugenol acetate, 1'S-1'-hydroxychavicol acetate, p-hydroxycinnamaldehyde, p-coumaryl-diacetate, trans-coniferyl-diacetate, trans-p-coumaryl alcohol, trans-p-hydroxycinnamyl acetate, p-acetoxycinnamyl alcohol, p-hydroxybenzaldehyde, chavicol acetate, chavicol, methyl-eugenol, eugenol, eugenol acetate, methyl cinnamate; terpenes and related compounds, including monoterpenes and sesquiterpenes, such as 1,8-cineole, α-pinene, δ-pinene, α-terpineol, terpinen-4-ol or 4-terpineol, camphene, camphor, myrcene, (Z)-β-ocimene, limonene, linalool, fenchyl acetate, geranyl acetate, bornyl acetate, citronellyl acetate, 2-acetoxy-1,8-cineole, 3-acetoxy-1,8-cineole, guaiol, β-farnesene, β-bisabolene, (Z,E)-farnesol, β-caryophyllene, α-bergamotene.

In a preferred embodiment, the rhizomes of *A. galanga* or *A. conchigera* provided for preparing the dry preparation I are fresh rhizomes. The apical shoots may be removed, or the rhizomes may still comprise at least one apical shoot. The stems may be removed, or the rhizomes may still comprise at least one stem. In one embodiment, the harvested rhizomes are stored frozen at a temperature between −20 and 0° C. until drying. In other embodiments, the harvested rhizomes are stored at a temperature between 0 and 25° C. until drying, such as at a temperature between 0 and 20° C., such as at a temperature between 0 and 15° C., such as at a temperature between 0 and 10° C., preferably at a temperature between 0 and 5° C. The rhizomes may be intact, or preferably cut or sliced prior to drying, for example they may be cut longitudinally in order to increase the exposed surface of the rhizomes, thus facilitating the drying process.

The dry preparation I contains preferably at least 1% 1'S-1'-acetoxychavicol acetate, such as at least 1.5% 1'S-1'-acetoxychavicol acetate, such as at least 2% 1'S-1'-acetoxychavicol acetate, such as at least 2.5%, such as at least 3%, such as at least 3.5%, such as at least 4%, such as at least 4.5%, such as at least 5%, such as at least 5.5%, such as at least 6%, such as at least 6.5%, such as at least 7%, such as at least 7.5%, such as at least 8%. Without being bound by theory, the inventors hypothesise that the contents of ACA are indicative of the contents of the components of *A. galanga* or *A. conchigera* which are prone to hydrolysis and/or degradation.

The freeze-drying may be performed at temperatures greater than 25° C. Preferably, the drying process comprises the steps of:
i) Freezing the rhizomes to a temperature of about −18 or −20° C.;
ii) Applying vacuum until the pressure is stable and in the range of 1.5 to 1.7 mb; the pressure may be maintained stable by supplying e.g. nitrogen;
iii) Increasing the temperature to start the drying process;
iv) Drying at a given temperature;
v) Eliminating the vacuum.

Thus, freeze-drying comprises the steps necessary to allow sublimation of the water comprised in the material to be freeze-dried, i.e. the rhizomes. The drying temperature applied in step iv) is above 0° C., such as up to 10° C., up to 20° C., up to 30° C., up to 40° C., up to 50° C., up to 60° C., up to 70° C., up to 80° C., up to 90° C. The drying temperature applied in step iv) may preferably be greater than 25° C., such as 30° C., such as 37° C., such as 40° C., such as 47° C., such as 50° C., such as 52° C., such as 60° C., such as 70° C., such as 80° C., such as 90° C.

In some embodiments, the freeze-dried rhizomes have a water content less than 15%, such as less than 14%, such as less than 13%, such as less than 12%, such as less than 11%, such as less than 10%, such as less than 9%, such as less than 8%, such as less than 7%, such as less than 6%, such as less than 5%.

It will be obvious to the skilled man that the temperatures and the durations used for each of the steps involved in the freeze-drying may vary depending e.g. on parameters such as the performance of the oven, on the pressure used, on the age of the rhizomes, on the extent of chopping or cutting of the roots.

In some embodiments, the method may further comprise milling the dry preparation I by methods known in the art, resulting in a powder.

The milling of the dry preparation I is preferably performed at a temperature suitable for preventing hydrolysis of volatile compounds such as ACA. Thus milling is preferably performed at a temperature lower than 50° C., such as lower than 40° C., such as lower than 35° C., such as lower than 30° C. Without being bound by theory, the inventors hypothesize that high temperatures may accelerate hydrolysis of ACA in the freeze-dried rhizomes, which still contain some water. Thus milling is preferably performed on a miller equipped with a cooling system in order to maintain the temperature within a suitable range despite the milling process being exothermic.

In some embodiments, the milling step comprises at least one step of down-sizing. The down-sizing may be performed in a miller equipped with a screen, wherein the screen has an opening smaller than 15 mm, such as 12 mm, such as 10 mm, such as 5 mm, such as 4 mm, such as 3 mm, such as 2 mm, such as 1 mm.

In some embodiments, the at least one step of down-sizing is three steps of down-sizing performed in the following order:
i) down-sizing on a 12 mm screen;
ii) down-sizing on a 2 mm screen;
iii) down-sizing on a 1 mm screen.

Performing multiple steps of down-sizing may facilitate the down-sizing process by first sorting out the bigger particles, whereby further down-sizing of the selected particles is easier.

In some embodiments, the resulting down-sized powder thus comprises particles having a size smaller than the smallest size of any screen used in the down-sizing process. It will be obvious to the skilled person that the choice of the screen depends on the desired particle size. The step of milling and/or the at least one step of down-sizing preferably result in a substantially homogenous dry preparation I, wherein the components of the rhizomes of *A. galanga* or *A. conchigera* are substantially evenly distributed.

In some embodiments, the dry preparation I is substantially homogenous.

In a preferred embodiment, the dry preparation I is formulated as an ingestible preparation, such as, but not limited to, a tablet, a pill, a capsule or a powder. It may also be formulated as a food additive or as a dietary supplement, a medical food or food for special medical purpose. The methods for formulating the dry preparation I may be any method known by the skilled man. The formulation may comprise other ingredients and may comprise coating.

In some embodiments, any additional formulation steps are performed at a temperature lower than 50° C., such as lower than 40° C., such as lower than 35° C., such as lower than 30° C.

The dry preparation I of *A. galanga* or *A. conchigera* may be obtained by the above method, further comprising the steps of: i) transferring the dry preparation to a gas-tight sealed container, said container containing an oxygen-free gas; ii) optionally, heating said container at a temperature comprised between 50° C. and 90° C., such as between 60° C. and 80° C., such as between 70° C. and 80° C., such as at 75° C. The oxygen-free gas may be nitrogen, or any other oxygen-free gas which will prevent growth of aerobic microorganisms. The dry preparation I should be stored in the container for a duration such that the titres in aerobic microorganisms, whether facultative or mandatory aerobes, are greatly decreased. For example, the dry preparation I is stored in the container containing oxygen-free gas for a duration of at least 5 days, such as at least 6 days, such as at least 7 days, such as at least 8 days, such as at least 9 days, such as at least 10 days, such as at least 11 days, such as at least 12 days, such as at least 13 days, preferably for at least 14 days, such as 15 days, such as 16 days.

The gas-tight sealed container containing the oxygen-free gas and the dry preparation I of *A. galanga* or *A. conchigera* may further be heated at a temperature comprised between 50° C. and 90° C., such as between 60° C. and 80° C., such as between 70° C. and 80° C., such as at 75° C. to ensure that growth of the remaining aerobic microorganisms and growth of the anaerobic microorganisms is inhibited. The container may be heated for a duration such that the total bacterial count in the dry preparation I is low. Surprisingly, such heating does not cause low ACA recovery in the dry preparation (see example 1).

Other methods known in the art may be used to reduce the total bacterial counts in the dry preparation I, such as, but not limited to: chemical sterilisation, irradiation, gas sterilisation, high pressure.

Specific embodiments of the invention have total bacteria counts such that ingestion of the present dry preparation I is regarded as safe and non-hazardous. For example, *Salmonella* species should be absent from a 25 g sample of the preparation, as recommended in general food safety guidelines (Guidelines on the Evaluation of Pathogenic Microorganisms in Food, Ministry for Food, Agriculture and Fishing, Denmark, 1999; Regulation (EC) No 2160/2003 of the European Parliament and of the Council of 17 Nov. 2003 on the control of *Salmonella* and other specified food-borne zoonotic agents). *Escherichia coli* counts should be within the acceptable range of less than 100 per g of preparation. Such preparations are considered essentially devoid of microorganisms.

Also provided herein is a method for preparing a granulate powder of *Alpinia galanga* or *Alpinia conchigera*, said method comprising the steps of:
i) providing a dry preparation of *Alpinia galanga* or *Alpinia conchigera*;
ii) binding said dry preparation with a binder solution comprising a binder dissolved in an essentially pure organic solvent, said binder solution being essentially devoid of water;
iii) removing the organic solvent; wherein steps ii) and iii) are performed at a temperature lower than 50° C., such as lower than 40° C., such as lower than 35° C., such as 30° C.

Examples of suitable binders include, but are not limited to: saccharides and derivatives thereof: disaccharides, e.g. sucrose or lactose, polysaccharides and derivatives thereof, e.g. starches, cellulose or modified cellulose such as microcrystalline cellulose and cellulose ethers such as hydroxypropyl cellulose (HPC); sugar alcohols and derivatives thereof, e.g. xylitol, sorbitol or maltitol; proteins, e.g. gelatin; synthetic polymers, e.g. polyvinylpyrrolidone (PVP), polyethylene glycol (PEG). Preferably, the binder is a solution binder. In one embodiment, the binder is PVP, for example PVP90.

Suitable organic solvents include solvents which are essentially pure and devoid of water. Without being bound by theory, the inventors believe that it is important that the solvent is devoid of water in order to prevent hydrolysis of ACA and other compounds of *Alpinia galanga* or *Alpinia conchigera*.

In some embodiments, the organic solvent is ethanol or isopropanol. It will be understood that any organic solvent capable of dissolving a binder to obtain a suitable binder solution can be used.

The skilled person will know in which mass ratio the binder should be dissolved in the organic solvent. Thus in some embodiments, suitable solvent/binder_mass ratios are comprised between 80:20 and 98:2, such as 85:15 and 96:4, such as 87:13 and 94:6, such as 89:11 and 92:8, such as 91.5:8.5.

In some embodiments, the organic solvent is at least 90% pure, such as at least 95% pure, such as at least 96% pure, such as at least 97% pure, such as at least 98% pure, such as at least 99% pure, such as 99.5% pure, such as 100% pure. Thus in some embodiments the organic solvent is ethanol which is at least 90% pure, such as at least 95% pure ethanol, such as at least 96% pure ethanol, such as at least 97% pure ethanol, such as at least 98% pure ethanol, such as at least 99% pure ethanol, such as 99.5% pure ethanol, such as 100% pure ethanol. In other embodiments the organic solvent is isopropanol which is at least 90% pure, such as at least 95% pure isopropanol, such as at least 96% pure isopropanol, such as at least 97% pure isopropanol, such as at least 98% pure isopropanol, such as at least 99% pure isopropanol, such as 99.5% pure isopropanol, such as 100% pure isopropanol.

The skilled person will know in which mass ratio the dry preparation is dissolved in the binder solution. In some embodiments, the dry preparation and the binder are contacted at a mass ratio comprised between 80:20 and 98:2, such as 85:15 and 96:4, such as 87:13 and 94:6, such as 89:11 and 93:7, such as 92.5:7.5.

Preferably, at least one of steps ii) and iii) is performed at a temperature of 30° C. or less. Generally, it is preferable to perform at least one of these steps at a temperature where hydrolysis of ACA and other compounds of *Alpinia galanga* or *Alpinia conchigera* is reduced. Thus in some embodiments, at least steps ii) and iii) are performed at a temperature of 30° C. or less. In other embodiments, all of steps i), ii) and iii) are performed at a temperature of 30° C. or less.

The method for preparing a granulate powder of *Alpinia galanga* or *Alpinia conchigera* may further comprise a milling step.

The milling step is preferably performed at a temperature suitable for preventing hydrolysis of volatile compounds such as ACA. Thus milling is preferably performed at a temperature lower than 50° C., such as lower than 40° C., such as lower than 35° C., such as lower than 30° C. Without being bound by theory, the inventors hypothesize that high temperatures may accelerate hydrolysis of ACA in the freeze-dried rhizomes, which still contain some water. Thus milling is preferably performed on a miller equipped with a cooling system in order to maintain the temperature within a suitable range despite the milling process being exothermic.

In some embodiments, the milling step comprises at least one step of down-sizing. The down-sizing may be performed in a miller equipped with a screen, wherein the screen has an opening smaller than 15 mm, such as 12 mm, such as 10 mm, such as 5 mm, such as 4 mm, such as 3 mm, such as 2 mm, such as 1 mm.

In some embodiments, the at least one step of down-sizing is three steps of down-sizing performed in the following order:
i) down-sizing on a 12 mm screen;
ii) down-sizing on a 2 mm screen;
iii) down-sizing on a 1 mm screen.

Performing multiple steps of down-sizing may facilitate the down-sizing process by first sorting out the bigger particles, whereby further down-sizing of the selected particles is easier.

In some embodiments, the resulting down-sized granulate powder thus comprises particles having a size smaller than the smallest size of any screen used in the down-sizing process. It will be obvious to the skilled person that the choice of the screen depends on the desired particle size. The step of milling and/or the at least one step of down-sizing preferably result in a homogenous granulate powder, wherein the components of *A. galanga* or *A. conchigera* are evenly distributed.

The dry preparation provided in step i) may be a powder. The method for granulating such powder preferably results in a granulate with a higher density than the powder provided in step i). Thus in some embodiments, the granulate powder obtained by the method of the invention has a density greater than 12 g/100 mL, such as greater than 15 g/100 mL, such as greater than 20 g/100 mL, such as greater than 22 g/100 mL, such as greater than 25 g/100 mL, such as greater than 26 g/100 mL, such as 27 g/100 mL, such as 28 g/100 mL, such as 29 g/100 mL, such as 30 g/mL.

In some embodiments, the granulate powder has an angle of repose comprised between 30° and 50°, such as between 35° and 45°, such as between 36° and 43°, such as between 37° and 41°, such as between 38° and 40°, such as 39°.

The dry preparation provided in step i) may be obtained as described above using one of the methods of the present invention.

The present method may further comprise a step of coating the granulate with a coating agent. Suitable coating agents are known in the art. Water-based coating agents may be employed. Such coating agents do not appear to accelerate hydrolysis of ACA.

In some embodiments, the granulate obtained by the present method is substantially homogenous.

In other embodiments, all the steps of the method for preparing a granulate are performed at a temperature of 30° C. or less.

In another embodiment, the dry preparation I of *A. galanga* or *A. conchigera* comprises essentially all the non-volatile compounds of *A. galanga* or *A. conchigera*; and at least 1% 1'S-1'-acetoxychavicol acetate.

The dry preparation I is obtainable by the method described herein and is essentially devoid of living microorganisms. It may be formulated as an ingestible preparation, such as a tablet, a pill, a capsule or a powder, as a dietary supplement, a food additive, or a medical food or a food for special medical purpose.

The dry preparation I of *A. galanga* or *A. conchigera* may be used as a medicament or as a medical device.

The dry preparation I may be administered to a male subject for enhancing male fertility. The male subject is preferably a mammal, such as, but not limited to, a human or a domestic animal, for example a bull, a sheep, a pig, a horse, a dog or a cat.

The dry preparation I may be administered together with an extract II comprising compounds with anti-oxidative activity. The extract II may be an extract of mashed fruits of *Punica granatum* (pomegranate) or an extract of *Terminalla catappa* or of *Terminalla myriocarpa* or of *Combretum molle*. Such extract may be obtained by mashing the pericarp of the fruits, e.g. by mashing the remains of squeezed fruits essentially devoid of juice followed by extraction. Alternatively, whole fruits may be mashed or pulverised prior to extraction. In other embodiments, the dry preparation I is administered together with a plant extract II comprising at least 20% of punicalagins. In yet other embodiments, the plant from which the extract II is obtained is a plant selected from the group consisting of *Punica granatum, Terminalla catappa, Terminalla citrina, Terminalla oblongata* and *Lumnitzera racemosa*. In other embodiments, the plant extract II is obtainable from a plant selected from the group consisting of *Rosa rugosa, Rosa canina, Aronia melanocarpa, Aronia prunifoloia, Aronia mitschurinii, Euterpe oleracea, Vaccinium* spp., *Lycium barbarum, Lycium chinense*. The plant extract II may be obtained from *Terminalla* spp. or from any plant comprising compounds with anti-oxidative activity.

Plant Extract II

The plant extract II is obtainable by methods known in the art. The plant from which the extract II is obtained may be a plant selected from the group consisting of *Punica granatum, Terminalla catappa, Terminalla citrina, Terminalla oblongata* and *Lumnitzera racemosa*. In other embodiments, the plant extract II is obtainable from a plant selected from the group consisting of *Rosa rugosa, Rosa canina, Aronia melanocarpa, Aronia prunifoloia, Aronia mitschurinii, Euterpe oleracea, Vaccinium* spp., *Lycium barbarum, Lycium chinense*. The extract II may be obtained from the pericarp of *Punica granatum*, from the leaves of *Terminalia catappa*, from the fruits of *Terminalla citrina*, from the roots of *Terminalla macroptera*, from the leaves of *Terminalia myriocarpa*, from the leaves of *Terminalla oblongata*, from the leaves of *Combretum molle*, or from the leaves of *Lumnitzera racemosa*. The plant extract II may be extracted from any *Terminalla* spp. comprising compounds with anti-oxidative activity. Preferably, the extract is obtained from the pericarp of *Punica granatum*, e.g. by mashing and extracting the remains of squeezed fruits. The extract II is preferably a dry extract, such as a powder or a granulate. In some embodiments, the extract II may be obtained from the fruits of *Rosa rugosa, Rosa canina, Aronia melanocarpa, Aronia prunifoloia, Aronia mitschurinii, Euterpe oleracea, Vaccinium* sp., *Lycium barbarum, Lycium chinense*. Other methods of preparing an extract II well known in the art are also within the scope of the invention.

Specific embodiments relate to extracts II comprising at least 40% polyphenols. The extract II preferably further comprises at least 30% punicosides and/or at least 20% punicalagins.

Composition

The present compositions may be such that the ratio (w/w) between the dry preparation I and the extract II is comprised in the range of 10:1 to 1:10, preferably the ratio is 3:4., even more preferably the ratio is 1:4 or 1:5.

In one embodiment, the composition comprising a dry preparation I and an extract II comprising compounds with anti-oxidative activity is a composition comprising a dry preparation of *A. galanga* or *A. conchigera* and an extract of *Punica granatum*. In some embodiments the composition is administered to a subject with poor semen quality. Poor semen quality may be reflected by a low total motile sperm count (TMSC), such as a TMSC<15.times.10$^6$. Poor semen quality may also be reflected by low sperm motility. In some embodiments, administration of a composition comprising the present dry preparation I of *A. galanga* or *A. conchigera* and an extract II of pomegranate to a male subject results in increased semen quality, for example it results in increased TMSC and/or increased sperm motility and/or increased spermatogenesis. Increased sperm motility may be reflected by an improvement in the motility grade, such as an improvement from grade d to grade c, from grade c to grade b, from grade b to grade a.

Specific embodiments relate to the use of a composition as disclosed herein for enhancing male fertility by administration to a male subject for a duration of at least 30 days, such as at least 50 days, such as at least 100 days, such as at least 150 days. Preferably, the composition is administered at least until the subject has conceived offsprings.

Other embodiments relate to the use of a composition as disclosed herein for enhancing male fertility by administration to a male subject. Preferably, the dry preparation I in the composition is at a dosage of at least 100 mg preparation/day, such as at least 125 mg preparation/day, such as at least 250 mg preparation/day, such as between 250 and 3000 mg preparation/day, preferably at least 500 mg preparation/day, such as 225 mg preparation/day. Other embodiments relate to the use of a composition for enhancing male fertility by administration to a male subject at a dosage of at least 2 mg ACA/day.

In some embodiments, male fertility is enhanced by administration of a dry preparation I of *A. galanga* or *A. conchigera* and an extract II to a male subject. The extract II comprises preferably at least 40% polyphenols, at least 30% punicosides and/or at least 20% punicalagins. In some embodiments, the composition is administered to a male subject at a dosage of at least 75 mg punicalagins/day, such as between 75 mg/day and 600 mg/day, such as between 100 mg/day and 500 mg/day, preferably at least 300 mg/day. In some embodiments, the dosage of punicosides is at least 100 mg/day, such as between 100 mg/day and 800 mg/day, such as between 100 mg/day and 600 mg/day, preferably at least 400 mg/day. The dosage of polyphenols is at least 125 mg/day, such as between 125 mg/day and 1000 mg/day, such as between 123 mg/day and 700 mg/day, preferably at least 500 mg/day. In a preferred embodiment, the composition comprises a dry preparation I of *Alpinia galanga* rhizomes and an extract II of *Punica granatum* pomace.

The present composition may be formulated in a formulation, preferably an ingestible formulation, such as a medicament, a dietary supplement, a food additive or a medical food or a food for special medical purpose. The formulation may comprise other ingredients, such as, but not limited to, an excipient, a coating agent, a flavouring agent. The composition may be formulated as a tablet, a pill, a capsule, a powder or a granulate. Other formulations suited for the purpose will be obvious to the skilled man and are also envisioned. Preferably, the dry preparation I is homogenised prior to formulation of the composition. The composition may be formulated as distinct formulations, wherein the first device comprises the dry preparation I and the second device comprises the extract II. Alternatively, the composition may be formulated as a single formulation.

The present invention also relates to a method for increasing the quality of semen, said method comprising the step of administering a composition as described above to a male subject. The composition may be administered as an ingestible medicament, as a medical device, a dietary supplement, a food additive or a medical food or a food for special medical purpose. Preferably, the dry preparation I in the composition is at a dosage of at least 100 mg preparation I/day, such as at least 125 mg preparation I/day, such as at least 250 mg preparation Hay, such as between 250 and 3000 mg preparation I/day, preferably at least 500 mg preparation Hay, such as 225 mg preparation I/day. Other embodiments relate to the use of a composition for enhancing male fertility by administration to a male subject at a dosage of at least 2 mg ACA/day, such as between 5 and 50 mg ACA/day, preferably at least 10 mg ACA/day. The extract II comprises preferably at least 40% polyphenols, at least 30% punicosides and at least 20% punicalagins. In some embodiments, the composition is administered to a male subject at a dosage of at least 75 mg punicalagins/day, such as between 75 mg/day and 600 mg/day, such as between 100 mg/day and 500 mg/day, preferably at least 300 mg/day. In some embodiments, the dosage of punicosides is at least 100 mg/day, such as between 100 mg/day and 800 mg/day, such as between 100 mg/day and 600 mg/day, preferably at least 400 mg/day. The dosage of polyphenols is at least 125 mg/day, such as between 125 mg/day and 1000 mg/day, such as between 125 mg/day and 700 mg/day, preferably at least 500 mg/day. In a preferred embodiment, the composition comprises a dry preparation I of *Alpinia galanga* rhizomes and an extract II of *Punica granatum* pomace.

Also disclosed herein is a method for enhancing semen quality in a male subject with low or normal sperm quality. The subject may suffer from azoospermia, oligospermia, low total motile sperm count, low sperm motility. The male subject may be human. The invention is of particular interest for those men whose sperm quality is decreased as a consequence of lifestyle, for example because of smoking, high coffee consumption, stress, alcohol. In other embodiments, the male subject is selected from the group consisting of male domestic animals, especially animals for which the production of offspring may be strongly desirable, such as, but not limited to, a bull, a horse, a sheep, a pig, a rabbit, a dog or a cat.

In another aspect, the present compositions may be administered for preventing hypertension, hypotension, high density lipid oxidation, low density lipid oxidation, atherosclerosis, oxidative stress in the body, development of colds, urinary infections, bacterial, viral or fungi infections, impotence, weight variations, free radical-induced damage to DNA and cell membrane, for regulating testosterone and/or total androgen levels in the serum, for increasing endurance, mental or physical energy, for reducing mental stress, for increasing potency or sexual activity.

Based on the results shown in the examples below, the inventors hypothesise that a combination of ACA and polyphenolic compounds such as punicosides, including punicalagins and/or punicalins, induces health benefits such as preventing hypertension, hypotension, high density lipid oxidation, low density lipid oxidation, atherosclerosis, oxidative stress in the body, development of colds, urinary infections, bacterial, viral or fungi infections, impotence, weight variations, free radical-induced damage to DNA and cell membrane, for regulating testosterone and/or total androgen levels in the serum, for increasing endurance, mental or physical energy, for reducing mental stress, for increasing potency or sexual activity.

EXAMPLES

Example 1

Fresh rhizomes of *Alpinia galanga* were harvested and the stems growing from the rhizome were cut off at harvest 10-20 cm above the base. The apical shoots were left intact on the rhizome. The rhizomes were kept cool at all times (0-5° C.). Shortly prior to freeze-drying or freezing, the stems of the rhizomes were cut at the base and the rhizomes split longitudinally in order to facilitate the transfer of water vapours to the gas phase during the freeze-drying process. After the splitting process, the rhizomes were frozen at −18° C. until freeze-drying.

The rhizomes were freeze-dried under the following conditions:
Step 1:10 h at 47° C.
Step 2: 6 h at 52° C.
Step 3: 4 h decrease ramp to 37° C.
Step 4: 90 min at 37° C.
Step 5: Termination/elimination of vacuum The pressure was maintained at 1.5 mb by supplying nitrogen.

Microbiological counts were performed on the dried rhizomes after freeze-drying (table 1).

TABLE 1

Microbiological counts on dried rhizomes after freeze-drying.

| Tests | Method Ref. | Results | Units |
|---|---|---|---|
| MICROBIOLOGY REPORT | | | |
| T.V.C 30 ° c. 3 days | SM01 | 160000 | cfu/g |
| Coliforms I | SM02 | 150000 | cfu/g |
| E. coli | SM25 | 330 | cfu/g |
| B. cereus | SM11 | 201 | cfu/g |
| S. aureus | SM07 | <20 | cfu/g |
| C. perfringens | SM29 | <10 | cfu/g |
| Yeast | SM12 | 81000 | cfu/g |
| Mould | SM12 | <10 | cfu/g |

After drying, the water content in the *A. galanga* rhizome was 2-5%.

The dried rhizomes were then transferred to a gas- and aroma tight sealed foil bag and stored in an oxygen-free gas (Nitrogen) for 14 days in order to eliminate or decrease the presence of aerobic microorganisms.

Characteristics of the foil bag:
(WMPET12/DRY/LPDE Film 100) Total 114 μm foil thickness
Dimensions 720 mm(W)*1190 mm (L)
Manufacturer: Won Ji Canada Corp.

After storage, the gas- and aroma tight bags with dried rhizomes were transferred to a heating oven for 3 hours at 75±3° C. in order to further decrease the number of microorganisms in the product.

Microbiological counts were performed on the dried rhizomes after this step (table 3).

TABLE 2

Microbiological counts on dried rhizomes after storage in nitrogen for 14 days and heating for 3 hours at 75 ± 3° C.

| Analyse | Result |
|---|---|
| 56490 Aerobes, 30° C./3 d. | 280 |
| 56080 Yeast | <10 |
| 56079 Mould | <10 |
| 55106 *Salmonella* | neg/25 g |
| 56496 *E. coli* | <10 |
| 55304 Enterobacteriaceae | <10 |
| 56341 *List. monocytogenes* | neg/25 g |
| 55323 Koag. pos. Staph. | <10 |
| 92029 Pesticides SP201 | Not detected |
| 92030 Pesticides SP203 | Not detected |

After freeze-drying, storage in oxygen-free nitrogen atmosphere (<3% oxygen) and heating of the rhizomes in the foil bags, analytical tests of the ACA levels were performed after extraction with ethanol and subsequent GC-MS quantification. The level of ACA in the dry roots was 4.03% (with 3% water content in the rhizomes). An example of the GC-MS chromatogram of the quantification of ACA recovered from the freeze-dried AG rhizomes is presented in FIG. 1. Examples of GC chromatograms of extracts from a preparation of freeze dried *Alpinia galanga* rhizomes (FIG. 1) and fresh rhizomes (FIG. 2) clearly illustrate that ACA (1'S-1'-acetoxychavicol acetate) is the most abundant compound in *Alpinia galanga* rhizomes. Quantification was performed using a calibration curve for the external ACA standard (FIG. 3).

Example 2

*Alpinia galanga* root powder (2 g) (Commercial extract 2) was extracted with 10 ml dichloromethane in a closed Blue Cap flask (25 ml) overnight in the dark under stirring at room temperature. The filtered dichloromethane extract was analyzed directly by GC-MS (70 eV). The major peak in the chromatogram (not shown) at retention time 26.16 min has a molecular ion at m/z 164 and major fragment ions at m/z 131 and 133 (base peaks), which indicates that it is closely related to eugenol and/or chavicol. Search in the MS database gave no obvious candidates but its molecular ion and its fragments indicate that the compound could be 1-hydroxy chavicol methyl ether. Furthermore, it can be concluded that the extract contained only trace amounts of the characteristic marker compounds of *galanga* roots such as 1'S-1'-acetoxychavicol acetate (ACA), hydroxychavicol acetate (HCA) or 1'-S-1'-acetoxyeugenol acetate. Table 3 shows a comparative analysis of several *Alpinia galanga* preparations and their content in ACA.

TABLE 3

Comparative analysis of *A. galanga* preparations.

| Source | Marker | Method | Content |
| --- | --- | --- | --- |
| Commercial extract 1 | ACA | GC-MS | Traces |
| Commercial extract 2 | ACA | GC-MS | Traces |
| Rhizomes (prepared as described herein) | ACA | GC-MS | 4.03% |

Example 3

Here is shown an example of a formulation of the invention based on a dry preparation of *A. galanga* (table 4).

TABLE 4

| mg/pr tablet | Compound | Function |
| --- | --- | --- |
| 190,910 | Dried powder of *Alpinia galanga* prepared according to the procedures described above | Active ingredient |
| 18,000 | Talc (E553b) | |
| 194,300 | Cellulose, microcrystalline (E460) | |
| 54,270 | Syloid AL1 (E551) | |
| 4,00 | Magnesium steareate (E470b) | |
| 461,480 | Total core tablet | |
| 1,000 | Shellac (E904) | Part of the filmcoat |
| 0,010 | Copper complexes of Chlorophylls (E14i) | Part of the filmcoat - colouring agent |
| 0,621 | Propylene glycol (E1520) | Part of the filmcoat |
| 1,055 | Talc (E553b) | Part of the filmcoat |

TABLE 4-continued

| mg/pr tablet | Compound | Function |
| --- | --- | --- |
| 2,917 | Titanium dioxide (E171) | Part of the filmcoat |
| 3,103 | Pharmacoat 615 (Hydroxypropyl methyl cellulose) (E464) | Part of the filmcoat |
| 8,706 | Total film coat | |

Example 4

Table 5 shows an example of formulating tablets comprising a dry preparation of *A. galanga* and an ethanolic extract of *P. granatum* (pomace extract).

TABLE 5

| mg/pr tablet | Compound | Function |
| --- | --- | --- |
| 190,910 | Dried powder of *Alpinia galanga* prepared according to the procedures described ealier in this section | Active ingredient |
| 250,000 | Dried powder extract (ethanolic/water) of *Punica granatum* pomace (40% Punicosides) | Active ingredient |
| | Talc (E553b) | |
| | Cellulose, microcrystalline (E460) | |
| | Syloid AL1 (E551) | |
| | Cellulose, microcrystalline, magnesium stearate (E470b) | |
| | Total core tablet | |
| 1,000 | Shellac (E904) | Part of the filmcoat |
| 0,010 | Copper complexes of Chlorophylls (E14i) | Part of the filmcoat - colouring agent |
| 0,621 | Propylene glycol (E1520) | Part of the filmcoat |
| 1,055 | Talc (E553b) | Part of the filmcoat |
| 2,917 | Titanium dioxide (E171) | Part of the filmcoat |
| 3,103 | Pharmacoat 615 (Hydroxyoropyl methyl cellulose) (HPMC) (E464) | Part of the filmcoat |
| 8,706 | Total film coat | |

Example 5

Clinical Study

The effects of the administration of a dry preparation of *A. galanga* together with an extract of *P. granatum* on semen quality was investigated in male subjects in a randomized, double-blinded, placebo-controlled clinical study. The purpose of the study was to test the efficacy of treatment with the plant preparations compared with placebo. The study period lasted 3 months (90 days) in order to cover the full cycle of sperm production (72-74 days).

Inclusion and Exclusion Criteria

Study participants were recruited from Nordic Cryobank (rejected as sperm donors due to relatively low sperm counts), from the Fertility Clinic at Region Hospital Horsens, Denmark, and through advertising in local newspapers. Inclusion criteria were two baseline sperm samples each showing a total number of motile spermatozoa (TMSC) 5 $200 \times 10^6$. Potential study participants which fulfilled this requirement should then fill out a questionnaire about life style, former illness and medicine consumption to ensure that the reason for inferior semen quality was not due to obvious medicinal reasons, such as cryptorchidism or genital tract infection. Another exclusion criterion was azoospermia. Study participants were not examined by a medical doctor prior to the inclusion. Otherwise study participants must be at least 18 years old.

Upon termination of the study the participants completed another questionnaire in order to examine the occurrence of any negative or positive side effects.

Sample Collection

Semen samples were collected at Nordic Cryobank, Arhus, or at Region Hospital Horsens. Samples collected at Nordic Cryobank were stored at body temperature for a few hours before transport to Region Hospital Horsens where they were analysed.

Study Participants

Within the time schedule for the study, it was possible to recruit 70 men. Four of the men did not enter the study for unknown reasons. Of the remaining 66 participants, 11 men had a semen quality at baseline of TMSC≤40×10$^6$. Thus a minority of the included men had normal semen quality as defined by the TMSC.

Altogether 32 men received treatment while 34 men received placebo. One study participant in the treatment group had only one follow up value.

Randomization and Blinding

The randomisation unit was each individual. Study participants were randomized equally to treatment or placebo within blocks of 10.

Clinical investigator, laboratory technician, study participants and statistician were blinded.

Measurement

Semen quality was measured twice before initiation of the treatment with an interval of 4-10 days between the two measurements. The average of these two measurements was designated the baseline value. Semen quality was measured again 4-8 days after initiation of treatment in order to test if there was an acute effect of the treatment. Finally, semen quality was measured twice at the end of the treatment period (90 days) with an interval between the two measurements of 4-10 days.

The average of these two measurements was designated the follow-up value.

Primary Outcome

The primary outcome was change in semen quality expressed as the total motile sperm count (TMSC)/ejaculate during the study period. The TMSC is defined as: ejaculate volume.times.spermatozoa concentration.times.percentage of motile spermatozoa. These three parameters were measured according to the methods described in the WHO laboratory manual for the examination and processing of human semen, 5.sup.th Edition, WHO (2010). The primary outcome was calculated as the difference between the follow-up value and the baseline value. The difference between the treatment group and placebo group with respect to this outcome was analysed by an unequal variance t-test.

This test takes into account variance heterogeneity between the two groups and deviation from normal distribution. As a confirming analysis all confidence intervals and p-values were calculated by the bootstrap method.

Treatment Vs. Placebo

Both the treatment group and the placebo group had to take 2×4 tablets each day, 4 in the morning and 4 in the evening, if possible in combination with a meal.

The daily treatment consisted of 4 tablets with extract of *Punica granatum* and 4 tablets with *Alpinia galanga* (2 of each in the morning and 2 of each in the evening). One tablet with *P. granatum* contained 250 mg extract so that the total daily dose was 1 g. One tablet of *A. galanga* contained 191 mg pulverized material, so that the total daily dose was 764 mg. The participants received all the tablets at the beginning of the study in two separate containers. The participants in the placebo group also received all tablets in two different containers.

Daily Dose and Active Compounds of *P. granatum* Tablets

The daily dose of *P. granatum* extract was 1000 mg extract pr. day. The contents of major ellagitannins in the tablets were measured by HPLC-analyses with the following results:

1.8-2.8 mg ellagic acid/tablet; 7.4-11 mg ellagic acid/4 tablets (daily dose)

20-28 mg punicalagin A/tablet; 79-110 mg punicalagin A/4 tablets (daily dose)

61-85 mg punicalagin B/tablet; 243-340 mg punicalagin B/4 tablets (daily dose)

1.2 mg punicalin/tablet 4.7 mg punicalin/4 tablets (daily dose)

Standards of punicalagin A and B were purchased from Chromadex, while the standard of punicalin was purchased from Stanford Chemicals. The standard of ellagic acid was purchased from PhytoLab.

From these analysis results the content of the major ellagitannins in the extract can be calculated:

Punicalagin A: 7.9-11%

Punicalagin B: 24-34%

Thus the total content of punicalagin A+B is between 32% and 45%. This is accordance with information from the specification of the extract which states that the total content of punicalagin A+B in the extract is >30%.

Daily Dose and Active Compounds of *A. galanga* Tablets

The daily dose of galangal preparation was 763.64 mg pr. day corresponding to approx. 7 g of fresh rhizome of *A. galanga*.

The content of ACA in the tablets was measured by GC/MS-analysis with the following result:

3.9 mg ACA/tablet; 16 mg ACA/4 tablets (daily dose)

The standard of ACA was purchased from PhytoLab.

The content of ACA in the tablets was diminishing over time as shown in table 6. ACA is a semivolatile phenylpropanoid. At high temperatures, ACA may be partly or fully converted to 1-hydroxychavicol acetate and/or p-acetoxycinnamic alcohol and/or p-coumaryl diacetate.

TABLE 6

The reduction in ACA-content (%) of the tablets as a function of elapsed time after production.

| | Months after production | | | |
|---|---|---|---|---|
| | 1 | 5 | 12 | 21 |
| Reduction in ACA-content (%) | 0 | 22 | 35 | 48 |

The last analysis value at 21 months was the average of tablets from two different containers stored at different temperatures (approx. 5.degree. C. and room temperature, respectively). Storage temperature did not seem to affect the ACA-loss of the tablets.

Content of *P. granatum* Tablets

The *P. granatum* tablets contained the following ingredients (per tablet): 250 mg *P. granatum* extract standardized to 40% punicosides (the ellagitanins punicalagins and punicalins). A 40% ethanolic extraction of mashed *P. granatum* pomace (15-20:1) was followed by spraydrying.

2.55 mg silicon dioxide (E 551)
75 mg sodium bicarbonate (E 500ii)
122.2 mg microcrystalline cellulose (E 460)
5 mg Syloid AL1 (E 551)
5.25 mg magnesium stearate (E 470b)
Content of *A. galanga* Tablets The *A. galanga* tablets contained the following ingredients (per tablet):
190.91 mg pulverized *A. galanga*
18.00 mg talc (E 553b)
194.30 mg microcrystalline cellulose (E 460)
54.27 mg Syloid AD (E 551)
4.00 mg magnesium stearate (E 470b)
Content of Placebo Tablets (*P. granatum*)

The placebo tablets matching the *P. granatum* tablets consisted of the following ingredients (per tablet):
167.6 mg sodium bicarbonate (E 500ii) 296.6 mg microcrystalline cellulose (E 460)
2.35 mg Syloid AL1 (E 551)
5.15 mg magnesium stearate (E 470b)
Content of Placebo Tablets (*A. qalanga*)

The placebo tablets matching the *A. galanga* tablets consisted of the following ingredients (per tablet):
460.85 mg microcrystalline cellulose (E 460)
6.00 mg Syloid AL1 (E 551)
5.15 mg magnesium stearate (E 470b)
Coating All tablets were coated with a white film coat consisting of the following compounds (per tablet):
1,000 mg shellac (E 904)
0.621 mg propylene glycol (E 1520)
1.055 mg talc (E 553b)
2.917 mg titanium dioxide (E 171)
3.103 mg hydroxypropyl methyl cellulose (E 464)

Furthermore, the *A. galanga* tablets and matching placebo tablets were coloured with the following food colouring:
0.01 mg copper complexes of chlorophylls (E 141i).
Results Administration of a combination of a newly developed composition of *Alpinia galanga* and *Punica granatum* induced an average 62% increase (P=0.026) in TMSC for men with inferior semen quality following 90 days of treatment (Table 7). In the first half of the study where the content of ACA in the *A. galanga* composition was highest, the average increase in sperm counts was 74% (P=0.045) (Table 7). No effects on the sperm counts were observed after only 1 week of treatment (Table 7), indicating that the observed positive effects can be explained by a positive influence on spermatogenesis rather than an antioxidative protection of the mature sperm cells prior to or after ejaculation.

The increases in TMSC from baseline to follow up for each participant in the plant group and placebo group are shown in FIG. 4.

Example 6

Analysis of a number of dry *A. galanga* extracts sold as raw material for food supplements showed very low or no ACA content in the products analyzed. The ACA content in fresh rhizomes is relatively high (up to 11% DW). It is possible that the considerable, or in some cases, total, loss of ACA in the final products, may be caused by either 1) one or more of the methodological steps converting the fresh rhizomes to dry powders suitable for incorporation in tablets and/or 2) loss during storage prior to or after the preparation of the dry extracts or tablets.

Breakdown of the major active compound in *A. galanga*, ACA, may be initiated by hydrolysis in the presence of water and raised temperatures.

Further, our initial tests on the preparations of A. galangal produced by milling the freeze dried rhizomes into powder, showed, that the fibers of the rhizome have a different density and structure than the remainder components produced by the milling process. It was not possible to incorporate this inhomogeneous mixture of light fibers and heavier components evenly into tablets, i.e., the first tablets produced would have a higher proportion of the heavier fragments compared to those produced at the end of the tablet production process because the smaller and heavier fragments would move to the bottom of the funnel feeding the material into the tablet machine.

In order to obtain an even distribution of fibers and other fractions in the tablets a water-free and low-temperature method for granulation of the dry preparation was developed.

Prior to freeze-drying, the rhizomes were split or chopped as described above.

Subsequently, the split or chopped freeze-dried rhizomes were milled on a Co-mill equipped with air cooling system in order to avoid heating of the rhizomes during the grating process. The tough fibres present in the rhizomes cause significant friction in the grating process. Our initial experiments showed that the temperature in the powder would reach 50° C. or more which is expected to accelerate the hydrolysis of ACA. We therefore applied a standard air cooling system to the miller which kept the temperature below 30° C. GC quantification of the ACA content showed no significant loss of ACA following milling using the cooling system and the following sequence of down-sizing on a series of screens: first a 12 mm screen, then a 2 mm

TABLE 7

Average of total motile sperm counts for the two treatment groups
A = *Alpinia galanga* + *Punica granatum*, B = placebo

|  | Treatment | | | |
| --- | --- | --- | --- | --- |
|  | A (n = 32) | B (n = 34) | Difference | P-value |
| Baseline | 23.4 (14.3; 32.4) | 19.9 (12.0; 27.8) | 3.5 (−8.3; 15.3) | 0.56 |
| Initiating treatment | 23.6 (14.4; 32.8) | 20.1 (12.1; 28.1) | 3.5 (−8.4; 15.4) | 0.56 |
| Follow-up | 37.8 (23.6; 52.1) | 23.9 (14.2; 33.6) | 14.0 (−3.0; 30.9) | 0.10 |
| Initiating treatment - baseline | 0.2 (−1.9; 2.4) | 0.2 (−3.3; 3.6) | 0.1 (−4.0; 4.1) | 0.98 |
| Follow-up - baseline | 14.5 (6.8; 22.1) | 4.0 (−1.3; 9.3) | 10.5 (1.3; 19.7) | 0.026 | screen and finally a 1 mm screen. The distribution of particle sizes using this series of screens is presented in table 8.

TABLE 8

Distribution of particle sizes following milling with three down-sizing steps using initially a 12 mm screen, then a 2 mm screen and finally a 1 mm screen.

| Particle size, µm | Distribution, percent |
|---|---|
| 2000-1000 | 0.10 |
| 1000-500 | 28.90 |
| 500-250 | 35.90 |
| 250-125 | 21.40 |
| 125-63 | 12.00 |
| 63-45 | 1.70 |
| <45 | 0.0 |
| Total | 100 |

As mentioned above, the powder needs to be brought into a homogeneous mixture with higher density in order to be incorporated into tablets.

For this purpose a standard procedure in the industry has been to apply a binder (e.g. Polyvinylpyrrolidone) dissolved in a relatively high percentage of water and e.g. organic solvent such as ethanol. We developed a procedure dissolving the binder (7.5% Polyvinylpyrrolidone (PVP 90)) in 99.5% ethanol in order to reduce hydrolysis of ACA. Further the temperature was decreased to 30° C. This is important as there is still some water present in the freeze-dried roots, which may hydrolyse ACA or other compounds. The granulation process took place in vacuum at 40-50° C. After granulation, the solvent was dried off under vacuum at a temperature lower than 30° C. This caused no significant loss of ACA.

PVP90 was dissolved in 99.5% ethanol (91.5% w/w ethanol, 8.5% w/w PVP90). A dry preparation of *A. galanga* was mixed with PVP90 as binder (92.5% w/w dry preparation, 7.5% w/w PVP90). Tablets were manufactured, each tablet weighing 457.50 mg, and containing 7.50 mg coating and 120 mg granulate (corresponding to 111 mg of the dry preparation).

The granulation process caused the density of the powder to increase from 12 g/100 ml to 27 g/100 ml (Angle of repose: 39°). The granulated powder was further milled on a Co-mil using a 1 mm screen. The granulated powder was now suitable for incorporation into tablets.

We compared the ACA content in the freeze-dried rhizomes with that of the powder (prior to granulation) and also with the ACA content following granulation. The ACA content in the three products was not statistically different (between 7.9% and 8.1%), showing that the processes described here, preserve the ACA content in the freeze-dried roots.

The granulated powder was incorporated into tablets using a standard procedure in the industry. This procedure caused no significant change in the ACA content of the granulated powder (between 7.9 and 8.1%).

REFERENCES

Islam, M. W., Zakaria, M. N. M., Radhakrishnan, R., Liu, X.-M., Ismail, A., Chan, K., and Al-Attas, A. (2000): Galangal (*Alpinia galanga* Willed.) and Black seeds (*Nigella sativa* Linn.) and sexual stimulation in male mice. Journal of Pharmacy and Pharmacology 52 (Suppl.), 278-278.

Leiva, K. P., Rubio, J., Peralta, F., and Gonzales, G. F. (2011): Effect of *Punica granatum* (pomegranate) on sperm production in male rats treated with lead acetate. Toxicol. Mech. Methods 21, 6, 495-502.

Qureshi, S., Shah, A. H., and Ageel, A. M. (1992): Toxicity Studies on *Alpinia-Galanga* and *Curcuma-Longa*. Planta Medica 58, 2, 124-127.

Turk, G., Sonmez, M., Aydin, M., Yuce, A., Gur, S., Yuksel, M., Aksu, E. H., and Aksoy, H. (2008): Effects of pomegranate juice consumption on sperm quality, spermatogenic cell density, antioxidant activity and testosterone level in male rats. Clinical Nutrition 27, 2, 289-296.

The invention claimed is:

1. A composition suitable for formulation into tablets or capsules comprising:
   i) granulate composition I prepared from rhizomes of *Alpinia galanga* or *Alpinia conchigera*, said granulate composition comprising at least 2% 1'S-1'-acetoxychavicol acetate, said granulate composition being substantially homogeneous, and said granulate composition comprising essentially all the semi-volatile and non-volatile compounds of said rhizomes; and
   (ii) a plant extract II comprising compounds with antioxidative activity obtainable from a plant selected from the group consisting of *Punica granatum*, *Terminalia catappa*, *Rosa rugosa*, *Rosa canina*, *Euterpe oleracea*, *Vaccinium* sp., and *Lycium barbarum*.

2. The composition according to claim 1, wherein the granulate composition I comprises at least 3% 1'S-1'-acetoxychavicol acetate, preferably at least 4%, such as at least 4.5%, such as at least 5%, such as at least 5.5%, such as at least 6%, such as at least 6.5%, such as at least 7%, such as at least 7.5%, such as at least 8%.

3. The composition according to claim 1, wherein the ratio (w/w) between the granulate composition I and the extract II is comprised in the range of 10:1 to 1:10.

4. The composition according to claim 3, wherein the ratio (w/w) between the granulate composition I and the extract II is in the range of 1:4 to 1:5, such as 1:4, such as 1:5.

5. The composition according to claim 1, wherein the granulate composition I has been granulated using a suitable binder, such as polyvinylpyrrolidone (PVP).

6. The composition according to claim 1, wherein the extract II is a dry extract, such as a powder or a granulate.

7. The composition according to claim 1, wherein the composition is formulated as a medicament, a medical device, a dietary supplement, a food additive or a medical food or a food for special medical purpose.

8. The composition according to claim 1, wherein the extract II comprises at least 40% polyphenols.

9. The composition according to claim 1, wherein the extract II comprises at least 30% punicosides.

10. The composition according to claim 1, wherein the extract II comprises at least 20% punicalagins.

11. The composition according to claim 1 for use in the treatment of male infertility caused by low sperm count and/or by low sperm motility, in which the composition is administrated at:
   a. a dosage of granulate composition I comprising at least 5 mg 1'S-1'-acetoxychavicol acetate/day, such as between 5 and 50 mg 1'S-1'-acetoxychavicol acetate/day and preferably at least 10 mg 1'S-1'-acetoxychavicol acetate/day, and
   b. a dosage of plant extract II comprising at least 75 mg punicalagins/day, such as between 75 mg punicalagins/day and 600 mg punicalagins/day, such as between 100 mg punicalagins/day and 500 mg punicalagins/day, preferably at least 300 mg punicalagins/day.

12. The composition according to claim 11 for use in the treatment of male infertility, wherein the composition is administrated for a duration of at least 30 days, such as at least 50 days, such as at least 100 days, such as at least 150 days.

13. The composition according to claim 1, said composition being formulated as two distinct components, wherein the first component comprises the granulate composition I and the second component comprises the extract II.

14. A kit comprising a first container comprising a granulate composition I prepared from rhizomes of *Alpinia galanga* or *Alpinia conchigera*, said granulate composition comprising at least 2% 1'S-1'-acetoxychavicol acetate, said granulate composition being substantially homogeneous, and said granulate composition comprising essentially all the semi-volatile and non-volatile compounds of said rhizomes; and a second container comprising a plant extract II comprising compounds with anti-oxidative activity obtainable from a plant selected from the group consisting of *Punica granatum, Terminalia catappa, Rosa rugosa, Rosa canina, Euterpe oleracea, Vaccinium* sp., and *Lycium barbarum*.

15. The kit according to claim 14 for use in the treatment of male infertility caused by low sperm count and/or by low sperm motility.

16. The kit according to claim 14 wherein the first component contains at least 5 mg 1'S-1'-acetoxychavicol acetate/day, such as between 5 and 50 mg 1'S-1'-acetoxychavicol acetate/day and preferably at least 10 mg 1'S-1'-acetoxychavicol acetate/day, and the second component contains at least 75 mg punicalagins/day, such as between 75 mg punicalagins/day and 600 mg punicalagins/day, such as between 10 mg punicalagins/day and 500 mg punicalagins/day, preferably at least 300 mg punicalagins/day.

17. A method of treating male infertility caused by low sperm count and/or by low sperm motility, which method comprises administering to a male subject in need thereof an effective dose of the composition according to claim 1.

18. The method according to claim 17 of treating male infertility in which the composition is administrated to a male subject at:
 a. a dosage of granulate composition I comprising at least 5 mg 1'S-1'-acetoxychavicol acetate/day, such as between 5 and 50 mg 1'S-1'-acetoxychavicol acetate/day and preferably at least 10 mg 1'S-1'-acetoxychavicol acetate/day, and
 b. a dosage of plant extract II comprising at least 75 mg punicalagins/day, such as between 75 mg punicalagins/day and 600 mg punicalagins/day, such as between 100 mg punicalagins/day and 500 mg punicalagins/day, preferably at least 300 mg punicalagins/day.

19. The method according to claim 12, wherein the composition is administered for a duration of at least 30 days, such as at least 50 days, such as least 100 days, such as at least 150 days.

* * * * *

UNITED STATES PATENT AND TRADEMARK OFFICE
CERTIFICATE OF CORRECTION

PATENT NO. : 10,772,925 B2
APPLICATION NO. : 14/896122
DATED : September 15, 2020
INVENTOR(S) : Ina Giversen and Henrik Jakobsen Page 1 of 1

It is certified that error appears in the above-identified patent and that said Letters Patent is hereby corrected as shown below:

On the Title Page

In Column 1, at (30) Foreign Application Priority Data: Change 13171033 to "13171033.7"

Signed and Sealed this
Tenth Day of November, 2020

Andrei Iancu
*Director of the United States Patent and Trademark Office*